United States Patent
Cheng et al.

[11] Patent Number: 5,494,898
[45] Date of Patent: Feb. 27, 1996

[54] PEPTIDE SKELETAL MUSCLE RELAXANTS

[75] Inventors: Yea-Shun Cheng, Doylestown, Pa.; Zenon D. Konteatis, South Orange, N.J.; Mark J. Macielag, Branchburg, N.J.; David C. Palmer, Clinton, N.J.

[73] Assignee: Ohmeda Pharmaceutical Products Division Inc., Liberty Corner, N.J.

[21] Appl. No.: 303,975

[22] Filed: Sep. 9, 1994

Related U.S. Application Data

[63] Continuation-in-part of Ser. No. 210,242, Mar. 16, 1994, abandoned, which is a continuation of Ser. No. 59,229, May 6, 1993, abandoned, which is a continuation-in-part of Ser. No. 654,744, Feb. 13, 1991, abandoned.

[51] Int. Cl.$^6$ ............................................. A61K 38/06
[52] U.S. Cl. .............................. 514/18; 530/331; 530/345
[58] Field of Search .............................. 514/18; 530/331

[56] References Cited

U.S. PATENT DOCUMENTS 5,190,924   3/1993   Konteatis ................... 514/19

*Primary Examiner*—Jill Warden
*Assistant Examiner*—David Lukton
*Attorney, Agent, or Firm*—R. Hain Swope; Larry R. Cassett

[57] ABSTRACT

Novel diquaternary polypeptides possessing skeletal muscle relaxation activity represented by the formulae:

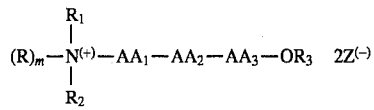

and

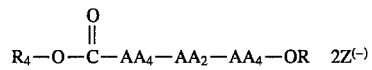

wherein: R is lower alkyl; $R_1$ and $R_2$ are lower alkyl or $R_1$ and $R_2$, together with the nitrogen to which they are attached form a heterocyclic ring having 5 to 7 member atoms; $R_3$ is lower alkyl, [N,N-di(lower alkyl)-3-piperidinium]$^{(+)}$, or [N,N-di(lower alkyl)-4-piperidinium]$^{(+)}$ $R_4$ is selected from the group consisting of t-butyl, benzyl or fluorenylmethyl; $A_1$ is selected from the group consisting of trans-4-acetoxyproline, phenylalanine, glutamic acid-γ-methyl ester, or proline; $AA_2$ is selected from the group consisting of phenylalanine, leucine, 3-(2-naphthyl)alanine, 3-(1-naphthyl)alanine, and 3-cyclohexylalanine; $AA_3$ is proline when $R_3$ is [N,N-di(lower alkyl)-3-piperidinium]$^{(+)}$ or [N,N-di(lower alkyl)-4-piperidinium]$^{(+)}$, and is Orn(δ-N$^{(+)}$—R—$R_1$—$R_2$) or Lys(ε-N$^{(+)}$—R—$R_1$—$R_2$) when $R_3$ ia lower alkyl; $AA_4$ is Orn(δ-N$^{(+)}$—R—$R_1$—$R_2$) or Lys(ε-N$^{(+)}$—R—$R_1$—$R_2$); $Z^{(-)}$ is a pharmaceutically acceptable anion; and $(R)_m R_1 R_2 N^{(+)}$ represents the acceptable anion; $(R)_m R_1 R_2 N^{(+)}$— represents the alpha amino group of $AA_1$; and m represents an integer of 0 or 1 with the proviso that m is zero only when $AA_1$ is trans-4-acetoxyproline or proline.

11 Claims, No Drawings

PEPTIDE SKELETAL MUSCLE RELAXANTS

Related Applications

This application is a continuation-in-part of U.S. patent application Ser. No. 08/210,242 filed Mar. 16, 1994, now abandoned, which, in turn, is a continuation of U.S. patent application Ser. No. 08/059,229 filed May 6, 1993, now abandoned, which, in turn, is a continuation-in-part of U.S. patent application Ser. No 07/654,744, filed Feb. 13, 1991, now abandoned.

This invention relates to novel diquaternary tripeptides useful as nondepolarizing skeletal muscle relaxants.

BACKGROUND OF THE INVENTION

Peptides comprised of a relatively low number of amino acid residues, yet which possess therapeutic activity, are known in the art. For example, Okai Japanese Patent No. 63-215697 (unexamined) discloses peptides containing at least five amino acid residues which are stated to have muscle relaxant activity. The type of muscle relaxant activity possessed by the disclosed peptides is not given.

Gieger, et al., U.S. Pat. No. 4,623,715, discloses peptides containing four or more amino acid residues, preferably pentapeptides and hexapeptides, which are useful as mood-elevators, antidepressants and anxiolytic agents.

Gormley, U.S. Pat. No. 4,421,744, discloses peptides and pseudo-peptides of the formula $(R)_2N-A-B-D-E-F-X$ wherein A and F are amino acid residues, and each of B, D and E can be an amino acid residue or a valency bond. These compounds are active as opiate receptor agonists.

Wilkinson, U.S. Pat. No. 4,254,106, discloses N,N-dialkyl, i.e. N-terminal tertiary, peptides containing at least five amino acid residues which are useful as morphine agonists.

Kahn et al. *Tetrahedron Letters*, Vol. 27, No. 40, pp 4841–4844, (1986), and Najjar, U.S. Pat. No. 3,778,426, disclose peptides which mimic the activity of the naturally occurring tetrapeptide tuftsin which is an immunostimulant.

Kouge et al. *Bulletin of the Chemical Society of Japan*, Vol. 60, pp 4343–4349 (1987) and Peptide Chemistry 1986. Proceedings of the 24th Japanese Symposium on Peptide Chemistry. T. Shiba ed. Osaka: Protein Research Foundation; pp. 229–232 (1987) disclose several tetrapeptides that contract and relax the anterior byssus retractor muscle of molluscs depending on the concentration administered. The peptides exhibit their modulatory effects by acting at specific presynaptic receptors in the molluscan muscle. In contrast, the known mammalian skeletal muscle relaxants act as agonists (depolarizing) or antagonists (non-depolarizing) at the postsynaptic nicotinic acetylcholine receptor.

Matsuo et al., U.S. Pat. No. 4,904,763, discloses several cysteine-bridged peptides, containing at least twenty amino acids, that induce relaxation of mammalian vascular smooth muscle.

Sakakibara, Chem. Abstr., Vol. 105:43332p and Chem. Abstr., Vol. 105:97955n disclose several dodeca-, trideca-, and tetradecapeptide derivatives of the conotoxins with skeletal muscle relaxant activity comparable to that of a tubocurarine derivative. The peptides contain at least two disulfide bridges which are necessary to lock the constituent amino acids in the proper conformation for bioactivity.

In accordance with the present invention, it has been found that certain tripeptides possess significant nondepolarizing muscle relaxant activity, thus making them useful therapeutically as skeletal muscle relaxants.

SUMMARY OF THE INVENTION

The present invention pertains to a method of producing a skeletal muscle relaxing effect in a mammal by the administration of an effective amount of a novel diquaternary peptide selected from those represented by the formulae:

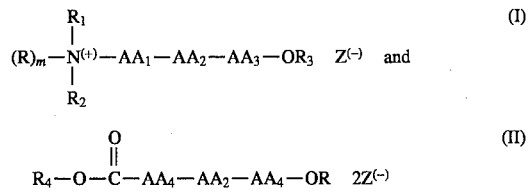

wherein:

m is 0 or 1;

R is lower alkyl;

$R_1$ and $R_2$ are lower alkyl or $R_1$ and $R_2$, together with the nitrogen to which they are attached form a heterocyclic ring having 5 to 7 member atoms;

$R_3$ is lower alkyl, [N,N-di(lower alkyl)-3-piperidinium]$^{(+)}$, or [N,N-di(lower alkyl)-4piperidinium]$^{(+)}$;

$R_4$ is selected from the group consisting of t-butyl, benzyl or fluorenylmethyl;

$AA_1$ is selected from the group consisting of trans-4-acetoxyproline, phenylalanine, glutamic acid-γ-methyl ester, or proline;

$AA_2$ is selected from the group consisting of phenylalanine, leucine, 3-(2-naphthyl)alanine, 3-(1-naphthyl)alanine, and 3-cyclohexylalanine;

$AA_3$ is proline when $R_3$ is [N,N-di(lower alkyl)-3-piperidinium]$^{(+)}$ or [N,N-di(lower alkyl)-4-piperidinium]$^{(+)}$, and is Orn(δ-N$^{(+)}$—R—$R_1$—$R_2$) or Lys(ε-N$^{(+)}$—R—$R_1$—$R_2$) when $R_3$ is lower alkyl;

$AA_4$ is Orn(δ-N$^{(+)}$—R—$R_1$—$R_2$) or Lys(ε-N$^{(+)}$—R—$R_1$—$R_2$);

$Z^{(-)}$ is a pharmaceutically acceptable anion; and $(R)_m R_1 R_2 N^{(+)}$ represents the alpha amino group of $AA_1$, with the proviso that m is zero only when $AA_1$ is trans-4-acetoxyproline or proline.

DETAILED DESCRIPTION OF THE INVENTION

The novel diquaternary peptide of the present invention are those represented by the formulae:

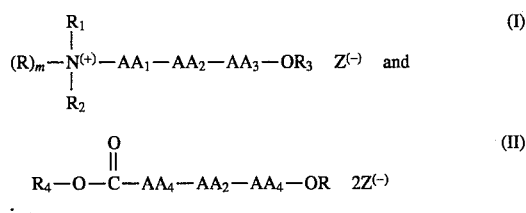

wherein:

m is 0 or 1;

R is lower alkyl;

$R_1$ and $R_2$ are lower alkyl or $R_1$ and $R_2$, together with the nitrogen to which they are attached form a heterocyclic ring having 5 to 7 member atoms;

$R_3$ is lower alkyl, [N,N-di(lower alkyl)-3-piperidinium]$^{(+)}$, or [N,N-di(lower alkyl)-4piperidinium]$^{(+)}$;

$R_4$ is selected from the group consisting of t-butyl, benzyl or fluorenylmethyl;

$AA_1$ is selected from the group consisting of trans-4-acetoxyproline, phenylalanine, glutamic acid-γ-methyl ester, or proline;

$AA_2$ is selected from the group consisting of phenylalanine, leucine, 3-(2-naphthyl)alanine, 3-(1-naphthyl)alanine, and 3-cyclohexylalanine;

$AA_3$ is proline when $R_3$ is [N,N-di(lower alkyl)-3-piperidinium]$^{(+)}$ or [N,N-di(lower alkyl)-4-piperidinium]$^{(+)}$ and is Orn(δ-$N^{(+)}$—R—$R_1$—$R_2$) or Lys(ε-$N^{(+)}$R—$R_1$—$R_2$) when $R_3$ is lower alkyl;

$AA_4$ is Orn(δ-$N^{(+)}$—R—$R_1$—$R_2$) or Lys(ε-$N^{(+)}$—R—$R_1$—$R_2$);

$Z^{(-)}$ is a pharmaceutically acceptable anion; and $(R)_m R_1 R_2 N^{(+)}$— represents the alpha amino group of $AA_1$, with the proviso that m is zero only when $AA_1$ is trans-4-acetoxyproline or proline.

In accordance with the present invention, the term "lower alkyl" is a branched or unbranched-hydrocarbon radical containing from 1 to 7 carbon atoms. Preferred lower alkyl groups in accordance with the subject invention are methyl and ethyl.

The amino acids which form the subject peptides will be referred to herein by their conventional abbreviations for the sake of brevity. Such abbreviations are well known to those skilled in the art. The primary abbreviations are given below:

| | |
|---|---|
| Leucine | Leu |
| Phenylalanine | Phe |
| Ornithine | Orn |
| Glutamic Acid Gamma Methyl Ester | Glu(γ-Me) |
| 1- and 2-Naphthylalanine | 1- and 2- Nal |
| Proline | Pro |
| Lysine | Lys |
| Cyclohexylalanine | Cha |

Preferred compounds within the scope of the present invention are those in the above formulae wherein R is methyl or ethyl. Wherein $R_1$ and $R_2$ are methyl or ethyl, or $R_1$ and $R_2$, together with the nitrogen to which they are attached, form a 5- to 7- member heterocyclic ring, such rings may contain additional hetero atoms, i.e. N or O (e.g. pyrrolidine, piperidine, hexamethyleneimine, piperazine, morpholine, and the like), $AA_2$ is phenylalanine, 3-(2-naphthyl)alanine or 3-(1-naphthyl)alanine, $AA_4$ is Lys(ε-$N^{(+)}$—R—$R_1$—$R_2$) and $R_4$ is t-butyl.

Another preferred group of diquaternary peptides within the scope of the present invention are those in the above formulae wherein m is O, $R_1$ and $R_2$ are methyl or ethyl, $AA_1$ is trans-4-acetoxyproline, $AA_2$ is phenylalanine, 3-(2-naphthyl)alanine or 3-(1-naphthyl)alanine, $AA_3$ is proline and $R_3$ is [N,N-di(lower alkyl)-3-piperidinium]$^{(+)}$ or [N,N-di(lower alkyl)-4-piperidinium]$^{(+)}$.

Unless it is specified herein that the amino acid moieties which make up the subject peptides are in the D-form or the L-form, both forms are intended. The abbreviation "Boc" used in reference to this group of compounds indicates t-butyloxycarbonyl.

Specific preferred peptide falling within the preceding two groups are the following:

Boc-Lys(ε-$N^+$—$Me_3$)-Phe-Lys(ε-$N^+$—$Me_3$)OMe 2Z$^-$

Boc-Lys(ε-$N^+$—$Me_3$)-Phe-Lys(ε-$N^+$—$Me_3$)OMe 2Z$^-$(all AA D-form)

Boc-Lys(ε-$N^+$—$Me_3$)-D-Phe-Lys(ε-$N^+$—$Me_3$)OMe 2Z$^-$

Boc-Lys(ε-$N^+$—$Me_3$)-2-Naphthala-Lys(ε-$N^+Me_3$)OMe 2Z$^-$

Boc-Lys[ε-Me—$N^+(CH_2)_5$—]-Phe-Lys[ε-Me—$N^+(CH_2)_5$—] OMe 2Z$^-$

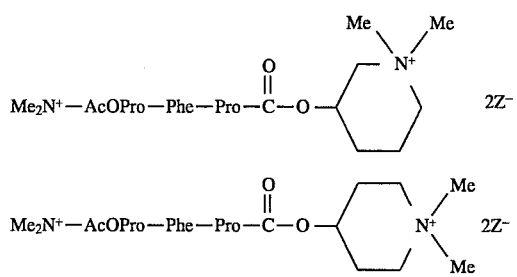

The pharmaceutically acceptable anions designated by Z$^-$in the above formula include, for example, inorganic anions such as the chloride, bromide, sulfate and the like, and organic anions such as the acetate, trifluoroacetate, oxalate, citrate, benzenesulfonate, tartrate and the like. Preferred anions are the chloride, the iodide, the trifluoroacetate and the benzenesulfonate.

Generally, the peptide skeletal muscle relaxants of the present invention may be prepared by solution phase peptide synthetic procedures analogous to those described hereinafter or methods known to those skilled in the art. For example, carboxylic moieties such as N-α-carbobenzyloxy (Cbz), N-α-fluorenylmethyloxycarbonyl(Fmoc), and N-α-t-butyloxycarbonyl(Boc) or substituted amino acid derivatives having suitable side chain protecting groups, if necessary, may be condensed with the amino functionality of a suitably protected amino acid or peptide using conventional coupling protocols such as dicyclohexylcarbodiimide (DCC), N-diethylamino-propyl-N'-cyclohexylcarbodiimide (EDCC) or 1-hydroxybenzotriazole (HOBt) in methylene chloride or dimethylformamide. Such coupling reactions are described, for example, in Meienhofer-Gross, *The Peptides*, Academic Press, Vol. 1, (1979) or Bodanszky-Bodanszky, *The Practice of Peptide Synthesis*, Springer-Verlag, (1984).

Following coupling reaction completion, the protectant moieties are removed as follows. The N-α-Boc moiety may be selectively removed with 50% trifluoroacetic acid (v/v) in methylene chloride. Neutralization of the resultant trifluoroacetate salt may be accomplished with a slight excess of triethylamine or diisopropylethylamine in methylene chloride. In the case of the N-α-Cbz moiety, selective removal is accomplished using hydrogen gas and a catalyst such as 5–10% palladium on carbon in a lower alkanol solvent such as methanol, ethanol or 2-propanol. Selective removal of the N-α-Fmoc moiety may be accomplished using 20% piperidine (v/v) in methylene chloride.

There is also provided in accordance with the invention a process for the manufacture of those of the compounds of formulae I and II which contain the groups: Orn(δ-$N^{(+)}$—R—$R_1$—$R_2$) or Lys(ε-$N^{(+)}$R—$R_1$—$R_2$); or R—$R_1$—$R_2 N^{(+)}$—$AA_1$—in combination with one of Orn(δ-$N^{(+)}$—R—$R_1$—$R_2$) and Lys(ε-$N^{(+)}$R—$R_1$—$R_2$) where R, $R_1$ and $R_2$ are lower alkyl, or $R_1$ and $R_2$, together with the nitrogen to which they are attached, form a heterocyclic ring having 5 to 7 member atoms, which comprises reacting the corresponding compound containing the group:

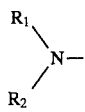

with a compound of the formula R-Hal wherein R is lower alkyl, and Hal is a halogen atom in a suitable solvent, for example, methanol, ethanol, acetonitrile or dimethyl formamide Precursors to the compounds formed in the preceding paragraph, i.e. compounds containing the group $R_1R_2N-$ wherein $R_1$ and $R_2$ are lower alkyl, or $R_1$ and $R_2$, together with the nitrogen to which they are attached, form a heterocyclic ring having 5- to 7- member atoms are prepared by reacting a compound containing the group $NH_2-$, generated either in situ by conventional deblocking methodology or from an isolated intermediate by reaction with the appropriate aldehyde or ketone and an alkali metal hydride reducing agent or hydrogen gas and a catalyst such as 5–10% palladium on carbon. The aldehyde or ketone may be, for example, formaldehyde, acetaldehyde, glutaraldehyde or acetone. The alkali metal hydride may be, for example, an alkali metal borohydride such as sodium cyanoborohydride. The process is conveniently carried out in a suitable solvent, such as methanol, optionally together with acetic acid or 1-hydroxyethylpiperazine ethanesulfonic acid (HEPES), at ambient temperature. The methods mentioned are described, for example, in Gormley, U.S. Pat. No. 4,421,744 (1983).

In addition, there is provided in accordance with the present invention, a process for the preparation of compounds of formulae (I) and (II) which contain the groups $R_1R_2N^{(+)}-AA_1-$ in combination with $-AA_3-OR_3$ or one of $Orn(\delta-N^{(+)}-R-R_1-R_2)$ and $Lys(\epsilon N^{(+)}R-R_1-R_2)$ where R, $R_1$ and $R_2$ are lower alkyl, where $AA_1$ is trans-4-acetoxyproline or proline and $R_3$ is [N,N-di(lower alkyl)-3-piperidinium]$^{(+)}$ or [N,N-di(lower alkyl)-4-piperidinium]$^{(+)}$ which comprises reacting the corresponding compound containing the groups:

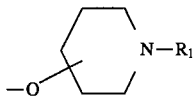

with a compound of the formula $R_2$-Hal, wherein Hal is a halogen atom, in a suitable solvent such as those given above.

Precursors to the compounds formed in the preceding paragraph, i.e. compounds containing the group $R_1-N-AA_1-$ wherein $R_1$ is lower alkyl and $AA_1$ is trans-4-acetoxyproline or proline are prepared by reacting a compound containing the group $HN-AA_1-$, generated either in situ by conventional deblocking methodology or from an isolated intermediate by reaction with the appropriate aldehyde and an alkali metal hydride reducing agent or hydrogen gas and a catalyst such as 5–10% palladium on carbon. The aldehyde may be, for example, formaldehyde, acetaldehyde or glutaraldehyde. The alkali metal hydride may be, for example, an alkali metal borohydride such as sodium cyanoborohydride. The process is conveniently carried out in a suitable solvent, such as described above.

Alternatively, compounds containing the groups $(R)_m(R)_1(R)_2N^{(+)}-AA_1-$, $Orn(\delta-N^{(+)}R-R_1-R_2)$ or $Lys(\epsilon-N^{(+)}R-R_1-R_2)$ where m=1 and R, $R_1$ and $R_2$ are lower alkyl are prepared by reacting a compound containing the group $NH_2-$ with a compound of the formula R-Hal, $R_1$Hal or $R_2$Hal wherein R, $R_1$, $R_2$ and Hal have the meanings stated above, in the presence of an acid-binding agent. A suitable acid-binding agent is, for example, an alkali metal carbonate or bicarbonate such as potassium carbonate or sodium bicarbonate. The process is conveniently carried out in a suitable solvent such as, for example, methanol, ethanol, acetonitrile or dimethylformamide. This method is described, for example, in Benoiton-Chen, *Proced. 14th Europ. Pept. Symp.*, (1976), p. 149.

The compounds of the present invention are administered parenterally, i.e. by intravenous, intramuscular or subcutaneous administration, in the form of an aqueous solution. The nonquaternary peptide are present in such preparations in the form of their pharmaceutically acceptable acid addition salts. Suitable carriers for the acid addition salts include isotonic water, sterile water for injection (USP), alone or in combination with other solubilizing agents such as ethanol, propylene glycol, or other conventional solubilizing agents known to those skilled in the art. A preferred carrier is an isotonic aqueous solution of the inventive compound.

Sterile solutions or suspensions of the compounds of the present invention preferably contain at least about 0.1% by weight of the active compound, but this amount may be varied to as much as about 50% by weight. The exact amount of the subject compound present in such compositions is such that a suitable dosage level will be obtained. Preferred compositions and preparations according to the present invention are prepared so that a parenteral dosage unit contains from between about 150 to about 1000 milligrams of a compound of formulae I or II.

The sterile solutions or suspensions prepared in accordance with the subject invention may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben; antioxidants, such as ascorbic acid or sodium metabisulfite, chelating agents such as ethylenediaminetetraacetic acid (EDTA); buffers, such as acetates, citrates or phosphates; and agents for the adjustment of tonicity, such as sodium chloride or dextrose. The parenteral preparations may be dispensed in ampules, disposable syringes, or multiple dose vials made of glass or plastic.

The compounds of the present invention can be administered to mammals, e.g., animals or humans, in amounts effective to provide the desired muscle relaxant therapeutic effect. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the unit dosage for a particular patient (man) can be as low as about 2 mg/kg, which the practitioner may titrate to the desired effect.

The peptide of the present invention are skeletal muscle relaxants of the competitive or nondepolarizing type (curariform). This type of muscle relaxant is preferred over the depolarizing agents, such as succinylcholine chloride, because they are easier to control. Nondepolarizing skeletal muscle relaxants antagonize the neurotransmitter action of acetylcholine by binding competitively with cholinergic receptor plates on the motor end plate. The subject compounds are advantageous in comparison with known nondepolarizing skeletal muscle relaxants, such as pancuronium bromide, cetacurium besylate and vecuronium bromide, in that they possess an onset of activity which is from three to five times more rapid. This advantageously rapid onset, coupled with an intermediate to short duration of activity, makes the subject compounds particularly useful as an adjunct to general anesthesia. The preferred polypeptides of the present invention are useful to facilitate short medical procedures such as endotrachial intubation, and for skeletal muscle relaxation during surgery or mechanical ventilation. These therapeutic indications are considered to be unexpected since, to Applicants' knowledge, there are no other peptides possessing this type of activity.

The following Examples illustrate this invention, it being understood that the invention is in no way intended to be limited to the details described therein. In the Examples, all parts and percentages are on a weight basis and all temperatures are in degrees Celsius, unless otherwise stated.

EXAMPLE 1

Tris-trifluoroacetate salt of N,N,N-Trimethyl-D-phenylalanyl-D-leucyl-D-(N-ε-trimethyl)lysine methyl ester.

A stirred solution of D-(N-ε-Cbz)lysine (1.0 g., 3.57 mmol) in methanol (25 ml) was cooled to 0° and treated dropwise with acetyl chloride (4.4 ml, 62 mmol). The ice bath was removed and, after stirring for 17 hours at room temperature, the reaction mixture was concentrated and then dried in vacuo to give 1.24 g. of a white, foamy solid. There was obtained D-(N-ε-benzyloxycarbonyl)lysine methyl ester, essentially pure by HPLC, gradient system: Buffer B, 0–100% in 30 minutes, flow rate 1 ml/min (Buffer A, 0.1% TFA in $H_2O$; Buffer B, Acetonitrile), on a RP C-18 Vydac column and UV detection at 214 nm. A single peak eluting at $R_t$ =15.59 min was observed.

The resulting product (1.17 g., 3.3 mmol) was dissolved in methylene chloride (5 ml) and DMF (10 ml) and cooled to 0° in an ice water bath. Triethylamine (0.5 ml, 3.6 mmol), 1-hydroxybenzotriazole (0.45 g., 3.3. mmol), N-α-t-butyloxycarbonyl-D-leucine (0.77 g., 3.3 mmol) and dicyclohexylcarbodiimide (0.687 g, 3.3 mmol) were added to the cooled solution. Stirring was continued for 7 hours during which the reaction mixture was allowed to warm to room temperature. The mixture was filtered and the precipitate washed with THF. The filtrate was concentrated in vacuo, and the residue taken up in EtOAc (200 ml) and washed with aqueous $NaHCO_3$, 1M HCl, aqueous $NaHCO_3$ and brine. The organic fraction was dried over $MgSO_4$ and concentrated to yield N-α-t-butoxycarbonyl-D-leucyl-D-(N-ε-benzyloxycarbonyl)lysine methyl ester as an amorphous residue weighing 1.58 g. HPLC showed only one peak at $R_t$ 24.0 min.

The ester prepared above (1.58 g., 3.12 mmol) was dissolved in methylene chloride (20 ml) and cooled in an ice water bath. Anisole (0.8 ml) and trifluoroacetic acid (TFA) (16 ml) were added, the reaction mixture was stirred at 0° for 2 hours and then concentrated to an oil. The oil was dissolved in water (150 ml) and washed with $Et_2O$ three times. The aqueous layer was lyophilized to give 0.51 g. of a white powder. The organic layer was backwashed with water and the new aqueous layer lyophilized to yield an additional 0.28 g of product. HPLC showed only one peak at $R_t$ =17.66 min.

The resulting product (0.51 g., 0.98 mmol) was dissolved in $CH_2Cl_2$ (5 ml) and DMF (5 ml), cooled in an ice water bath and treated with triethylamine (0. 14 ml, 1.05 mmol). α-Cbz-D-phenylalanine (0.29 g., 0.98 mmol), 1-hydroxybenzotriazole (0.13 g., 0.98 mmol) and dicyclohexylcarbodiimide (0.20 g., 0.98 mmol) were added to the stirred solution. The reaction mixture was allowed to warm to room temperature and stirred for a total of 17 hours. The solid product was filtered off, washed with THF and the filtrate concentrated. EtOAc (200 ml) was added to the filtrate which was then washed with aq $NaHCO_3$, 1 M HCl, aq $NaHCO_3$ and brine. The organic layer was dried over $MgSO_4$ and concentrated in vacuo to give 0.64 g. of N-α-benzyloxycarbonyl-D-phenylalanyl-D-leucyl-D- (N-ε-benzyloxycarbonyl)-lysine methyl ester as a white solid. TLC with 30:1 $CHCl_3$: MeOH showed only one product ($R_f$ =0.6).

To a solution of the resulting methyl ester (673 mg, 0.98 mmol) in methanol (100 ml) was added 10% Pd/C (210 mg in 2 ml of water). The mixture was hydrogenated in a Parr hydrogenation apparatus (Pi=50) for 7 hours, purged with N2 and the catalyst filtered off. The filtrate was concentrated in vacuo, taken up in methanol and concentrated again to give 410 mg of D-phenylalanyl-D-leucyl-D-lysine methyl ester as a white powder. HPLC indicated a major product at $R_t$ =13.14 min. together with a few minor impurities. The material was used as is.

The resulting product (0.41 g., 0.97 mmol) was dissolved in methanol (15 ml). To the solution was added $NaHCO_3$ (0.40 g., 4.76 mmol) and methyl iodide (6 ml, 96 mmol) and the reaction mixture was stirred at room temperature for 72 hours. The mixture was concentrated in vacuo to give 1.4 g. of a yellow solid. HPLC showed three peaks at $R_t$ =3.09 min. (HI), 13.39 min. (Product), and 16.67 min. (impurity).

The product was purified by RP-HPLC using Vydac C-18 one-inch column; gradient system: Buffer B, 0–100% in 30 min., flow rate 20 ml/min., UV detection at 220 nm (Buffer A, 0.1% TFA/$H_2O$; Buffer B, Acetonitrile). The pooled fractions were lyophilized to give 0.20 g. of tris-trifluoroacetate salt of N, N,N-trimethyl-D-phenylalanyl-D-leucyl-D-(N-ε-tri-methyl)lysine methyl ester as a white powder, pure by analytical HPLC, $R_t$=13.39 min.

The fast atom bombardment (FAB) MS of the product was consistent with the tris-trifluoroacetate salt of the desired product:

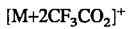

at m/z. Calc.: 732.8. Found: 732. Analysis calculated for $C_{28}H_{50}N_4O_4 \times CF_3CO_2H \times 2H_2O$: C, 46.26; H, 6.28: N, 6.35. Found: C, 46,31; H, 5.97; N, 5.93.

EXAMPLE 2

Methyl ester of N-α-t-butyloxycarbonyl-α-S-{4-[1-(1-methyl) piperidinium]butyl }glycyl-L-phenylalanyl-α-S-{4-[1-(1-methyl)piperidinium]butyl}glycine tris-trifluoroacetate.

A stirred solution of the methyl ester of (N-ε-benzyloxycarbonyl)-l-lysine hydrochloride (2.21 g., 6.7 mmol), N-α-t-butyloxycarbonyl-L-phenylalanine (2.0 g., 6.7 mmol), 1-hydroxybenzotriazole (HOBt) (1.81 g., 13.4 mmol), and 1-ethyl-3-(3-dimethylaminopropyl)carbodiimide hydrochloride (WSCl×HCl) (2.57 g., 13.4 mmol) in $CH_2Cl_2$ (30 ml), was cooled to 5° in an ice bath. Triethylamine (2.19 g., 21.6 mmol) was added via syringe maintaining the temperature at 5° After stirring for 2 hours, the reaction mixture was allowed to come to room temperature. The reaction mixture was stirred for 18 hours, washed with saturated $NaHCO_3$ solution, 1M HCl and brine and dried over magnesium sulfate. After removal of solvent in vacuo, the residue was triturated with ether/hexane to afford the methyl ester of N-ε-t-butyloxycarbonyl-L-phenylalanyl-L-(N-c-benzyloxycarbonyl)lysine as a white solid (3.2 g.). The structure was supported by NMR and IR.

The product (0.83 g., 1.57 mmol) was dissolved in methylene chloride (20 ml), cooled to 5° in an ice bath and treated with trifluoroacetic acid (TFA) (5 ml). The reaction mixture was stirred at room temperature for 1 hour, concentrated in vacuo and the residue triturated with diethyl ether to give an amorphous solid (0.85 g.). The NMR was consistent with the desired structure.

A solution of the above product (0.85 g., 1.53 mmol) in methylene chloride (10 ml) was cooled in an ice bath and treated with triethylamine (0.15 g., 1.53 mmol). After 30 minutes, the mixture was treated with N-α-t-butyloxycarbonyl-(N-ε-benzyloxycarbonyl)lysine (0.60 g., 1.53 mmol), 1-hydroxybenzotriazole (0.21 g., 1.53 mmol), and 1-ethyl-3-(3-dimethylaminopropyl) carbodiimide (WSCl×HCl) (0.29 g., 1.53 mmol). Triethylamine (0.15 g., 1.53 mmol) was added via syringe while maintaining the temperature of the reaction mixture at 5°. Stirring was continued for 2 hours after which the reaction mixture was allowed to come to room temperature. The reaction mixture was stirred for 18 hours, washed with saturated NaHCO$_3$ solution, 1M HCl, and brine, and dried over magnesium sulfate. After removal of solvent in vacuo, the residue was triturated with ether/hexane to afford the methyl ester of N-α-t-butyloxycarbonyl-(N-ε-benzyloxycarbonyl)-L-lysyl-L-phenylalanyl-L-(N-ε-benzyloxycarbonyl) lysine as a white amorphous solid (0.96 g.). The solid was dissolved in a minimum amount of diethyl ether and loaded onto a column of silica gel (50×5 cm). The column was eluted with diethyl ether/hexane (1/1)to isolate a less polar impurity followed by ether/hexane (4/1) to afford the fully protected tripeptide derivative. The pooled fractions were evaporated in vacuo to give the product as a white solid. The NMR was consistent with the desired structure.

To a solution of the methyl ester of N-α-t-butyloxycarbonyl-(N-ε-benzyloxycarbonyl)-L-lysyl-L-phenylalanyl-(N-g-benzyloxycarbonyl)-L-lysine(0.93 g., 1.15 mmol) in methanol (40 ml) and water (4 ml) contained in a Parr hydrogenation bottle was added 0.30 g. of 10% palladium on carbon. The resulting suspension was placed under hydrogen at 50 psi and shaken for 21 hours. The reaction mixture was filtered through celite and the filtrate concentrated to give the methyl ester of N-α-t-butyloxycarbonyl-L-lysyl-L-phenylalanyl-L-lysine bis-trifluoroacetate salt. The product was purified by RP-HPLC employing an 0.1% aqueous trifluoroacetic acid/acetonitrile linear gradient. The pooled fractions were lyophilized to give the product as a hygroscopic white solid (0.67 g.). The 'H-NMR is consistent with the desired structure. FAB mass spec. [M+H]$^+$m/z calc'd:= 535.7. Found: 537. Anal. calc'd. for C$_{27}$H$_{45}$N$_5$O$_6$× 2CF$_3$CO$_2$H×2H$_{O:}$ C, 46.56; H, 6.43; N, 8.76. Found: C, 46.83; H, 5.76; N, 8.53.

To a stirred solution of the above product (300 mg, 0.39 mmol) in acetonitrile (10 ml) was added 10 ml of 100 mM [4-(2-hydroxyethyl)-1-piperazine ethanesulfonic acid (HEPES) as buffer and 6 drops of bromocresol green as indicator, followed by 0.2 ml glutaric dialdehyde (50% wt. aqueous solution, 1.10 mmol) and sodium borohydride (400 mg., 10.6 mmol). The reaction mixture was stirred at room temperature for 3 hours maintaining the pH above 5.4. The solvent was removed in vacuo, the residue dissolved in 50 ml of methylene chloride and washed several times with 5% NaHCO$_3$. The organic phase was dried over MgSO$_4$, filtered and concentrated. The residue was purified by RP-HPLC using a linear gradient of 0.1% aqueous trifluoroacetic acid acetonitrile. The pooled fractions were lyophilized to give the methyl ester of N-α-butyloxycarbonyl-α-S- [4-(1-piperidino)butyl]glycyl-L-phenylalanyl-α-S-[4-(1 piperidino)butyl]glycine tris-trifluoroacetate as a white solid (95 mg). The 'H-NMR was consistent with the desired structure. FAB mass spec. [M+H]$^+$=672. Anal. calc'd. for C$_{37}$H$_{61}$N$_5$O$_6$×3CF$_3$CO$_2$H :C, 50.93; H, 6.36; N, 6.91. Found: C, 50.81; H, 6.60; 7.33.

To a stirred solution of the methyl ester of N-α-t-butyloxycarbonyl-αS-[4-(1-(piperdino)butyl]glycyl-L-phenylalanyl-αS-[4-(1-piperdino)butyl]glycine (300 mg, 0.45 mmol), prepared by passing a solution of the tris-trifluoroacetate salt in methanol (5 ml) through a short column of potassium carbonate, was added methyl iodide (5 ml, 80.3 mmol). After stirring at room temperature for 48 hours, the reaction mixture was concentrated and the residue purified by RP-HPLC employing a 0.1% aqueous trifluoroacetic acid/acetonitrile linear gradient. The pooled fractions were lyophilized to give the methyl ester of N-α-t-butyloxycarbonyl-α-S-{4-[1-(1-methyl)piperidinium]butyl}glycyl-L-phenylalanylα-S-{4-[1-(1-methyl)piperidinium] butyl}glycine tris-trifluoroacetate as a white solid (280 mg). The 'H-NMR was consistent with the desired structure. FAB mass spec. [M+2CF$_3$CO$_2^-$]$^{+=928}$. Anal. calc'd. for C$_{39}$H$_{67}$N$_5$O$_6$ ×CF$_3$CO$_2^-$×H$_2$O : C, 50.99; H, 6.66; N, 6.61. Found C, 51.01; H, 6.63; N, 6.65.

EXAMPLE 3

Tetrakis-trifluoroacetate salt of 1,1 ,-dimethyl-4-piperidyloxy ester of N,N-dimethyl-trans-4-acetoxy-L-prolyl-L-phenylalanyl-L-proline.

A suspension of 10% palladium on carbon in water (25 ml) was added to a suspension of trans-4-hydroxy-L-proline (6.576 g., 50.10 mmol) in methanol (100 ml) and 37% aqueous formaldehyde (16 ml, 213.5 mmol) in a Parr bottle. The bottle was pressurized to 50 psi with hydrogen and shaken overnight. The catalyst was removed by filtration through a pad of celite which was washed thoroughly with methanol (100 ml). Evaporation of the methanol and excess formaldehyde yielded N-methyl-trans-4-hydroxy-L-proline as a white solid which was recrystallized from methanol/diethyl ether to give 6.425 g. of white needles, m.p. 236°–238 ° (decomposition with gas evolution).

A suspension of the above product (7.286 g., 50.1 mmol) in glacial acetic acid (75 ml) was stirred and cooled in an ice bath during the dropwise addition of acetyl chloride (34.0 ml 478.2 mmol) in 25 min. The resulting thick cream suspension was allowed to warm to ambient temperature and stirred 7 hours. Evaporation of the glacial acetic acid and excess acetyl chloride gave a solid residue which was suspended in diethyl ether and filtered. The white solid was washed liberally with diethyl ether and dried to yield N-methyl-trans-4-acetoxy-L-proline hydrochloride (11.10 g.) mp 199°–202° (decomposition). The product was characterized by IR, NMR and MS. Anal. calc'd. for C$_8$H$_{13}$NO$_4$×HCl: C, 42.96; H, 6.31; N, 6.26. Found: C, 42.96; H, 6.42; N, 6.18.

Triethylamine (2.0 ml, 15.0 mmol) was added dropwise to a suspension of N-α-t-butoxycarbonyl-L-phenylalanine (1.325 g., 5.0 mmol) and L-proline benzyl ester hydrochloride in methylene chloride (20 ml), stirred and cooled to 0°. 1Hydroxybenzotriazole (0.975 g., 5.0 mmol) and 1-ethyl-3-(3dimethylaminopropyl)carbodiimide hydrochloride (1.032 g., 5.40 mmol) were added to the resulting clear solution.

The reaction mixture was allowed to warm to ambient temperature overnight. Methylene chloride (50 ml) was added and the organic solution washed sequentially with 5% NaHCO$_3$, 5% HCl and saturated brine. After drying over sodium sulfate, the organic solution was evaporated and the crude product purified by flash chromatography on silica gel using 1% methanol in chloroform. Pooled fractions were evaporated to yield 1.94 g. of N-α-t-butoxycarbonyl-L-phenylalanyl-L-proline benzyl ester as a white solid. The product was characterized by IR and NMR.

Trifluoroacetic acid was added to a cold (0°) solution of the above product (0.937 g., 2.15 mmol) in methylene chloride (20 ml). The reaction mixture was stirred for 1 hour at 0°, after which the methylene chloride and trifluoroacetic acid were evaporated. The residue (1.00 g., 2.15 mmol) and N-methyl-trans-4-acetoxy-L-proline hydrochloride (0.40 g., 2.15 mmol) were suspended in methylene chloride (10 ml) and cooled to 0°. Triethylamine (1.0 ml, 6.5 mmol) was added dropwise followed by 1-hydroxybenzotriazole (0.421 g., 2.74 mmol) and 1-ethyl-3-(3-dimethylaminopropyl) carbodiimide hydrochloride (0.5 g., 2.62 mmol). The reaction mixture was stirred for 24 hours and allowed to warm to ambient temperature. Methylene chloride (20 ml) was added to the reaction mixture and the organic solution washed sequentially with 5% sodium bicarbonate and saturated brine. After drying over sodium sulfate, the organic solution was evaporated and the resulting crude product, N-methyl-trans-4-acetoxy-L-phenylalanyl-L-proline benzyl ester trifluoroacetate purified by RP-HPLC using a Vydac C-18 one inch column; gradient system: Buffer A, 0.1% TFA/H$_2$O; Buffer B, acetonitrile, 0–100% in 30 min. with UV detection at 220 nm. Pooled fractions were lyophilized to give 0.693 g. of product as a white powder with R$_t$ =18.97 min. This product was characterized by IR, NMR and MS. The fast atom bombardment (FAB) MS of the powder showed (M+H) $^+$calc'd. 521.3. Found 522.

A suspension of 10% palladium on carbon (0.203 g.) in water (0.5 ml) was added to a solution of the above product (0.782 g., 1.23 mmol) in methanol (20 ml) in a Parr bottle. The bottle was pressurized to 45 psi with hydrogen and shaken at ambient temperature for 3 hours. The catalyst was removed by filtration through a pad of celite which was washed thoroughly with methanol (50 ml). Evaporation of the methanol afforded 0.547 g. of N-methyl-trans-4-acetoxy-L-prolyl-L-phenylalanyl-L-proline as a colorless oil.

Oxalyl chloride (0.325 ml, 3.73 mmol) was added to a cold (−10°) solution of the oil (0.79 g., 1.83 mmol) in a mixture of acetonitrile (20 ml) and dimethylformamide (1 ml) and the reaction mixture stirred for 30 min. A solution of 1-methyl-4-hydroxypiperidine (0.210 g., 1.83 mmol) in acetonitrile (2 ml) was added to the reaction mixture at −10° and the whole stirred an additional 30 min. at −10° after which the reaction mixture was warmed to ambient temperature during 14 hours. Methylene chloride (50 ml) was added to the reaction mixture which was washed successively with 5% sodium bicarbonate, saturated brine and water. The organic layer was dried over sodium sulfate and evaporated in vacuo to give a yellow oil which was purified by RPHPLC using a Vydac C-18 one-inch column; gradient system: Buffer A 0.1% TFA/H$_2$O; Buffer B, acetonitrile, 0–100% in 30 min. with UV detection at 220 nm. Pooled fractions were lyophilized to afford the tris-trifluoroacetate salt of 1-methyl-4-piperidyloxy ester of N-methyl-trans-4-acetoxy-L-prolyl-L-phenylalanyl-L-proline as a syrup with R$_t$=14.50 min. This product was characterized by IR, NMR and MS. The fast atom bombardment (FAB) MS showed (M+H)$^+$calc'd; 528.7. Found 529.0. Anal. calc'd. for C$_{28}$H$_{40}$N$_4$O$_6$ ×3CF$_3$CO$_2$H: C, 46.90; H, 4.98; N, 6.43. Found: C, 46.75; H, 5.03; N, 6.29.

A solution of the above product (0.266 g., 0.36 mmol) in methanol (10 ml) containing methyl iodide (3.0 ml, 48.2 mmol) was treated with sodium bicarbonate (0.344 g., 4.1 mmol) and the resulting suspension stirred at ambient temperature for 24 hours. The excess methyl iodide and methanol were evaporated in vacuo and the residue treated with acetone and filtered through celite to remove inorganic salts. The acetone was evaporated and the residue dissolved in 0.5% aqueous TFA and purified by RP-HPLC as described above. Lyophilization of pooled fractions gave the tetrakistrifluoroacetate salt of 1,1-dimethyl-4-piperidyloxy ester of N,N-dimethyl-trans-4-acetoxy-L-prolyl-L-phenylalanyl-L-proline monohydrate as a white powder (0.124 g.) with a R$_t$=13.25 min. This product was characterized by IR, NMR and MS. Analysis calculated for C$_{30}$H$_{46}$N$_4$O$_6$×2CF$_3$CO$_{H^×}$ $_{H_2}$O; C, 44.28; H, 4.89; N, 5.44. Found: C, 44.15; H, 4.67; N, 5.35.

EXAMPLE 4

The following bioassay methodologies were used to demonstrate the neuromuscular junction blocking activity of the compounds of the invention. The relaxant properties of compounds with this pharmacologic mechanism could be used during surgical anesthesia to facilitate endotracheal intubation and retraction of muscle groups as required to expedite access to various body cavities. Each of these tests extended the knowledge of the clinical potential of the subject compounds. In instances where the compounds of this invention were not subjected to analysis in a specific test, it is possible to estimate such activity based on known relationships to other clinically available drugs which had been tested.

The first step, in mice, establishes a preliminary estimate of the potency and efficacy of the compounds. The animals were placed on a screen, inclined 45° to the horizontal. Effective doses caused the mice to lose their grip and slide down the inclined screen. The dose in mg/kg of body weight required to inhibit grip strength in 100% of the mice tested in a dosage group is reported.

The type of muscle relaxation produced by the test compounds was then determined by injection into chicks. Compounds which cause competitive blockage of post-synaptic acetylcholine receptors, i.e. nondepolarizing drugs, produce a flaccid paralysis in the chicks whereas drugs which cause depolarization of the post-synaptic muscle membrane produce a rigid paralysis. Only those compounds shown by this test to be nondepolarizing are tested further. This test established that the subject compounds are nondepolarizing muscle relaxants. All compounds reported in the following tables were nondepolarizing in the chick assay.

The rabbit paw twitch analysis was used to demonstrate the rate of onset and duration and to confirm the range of potency of test compounds. In a large series of similar relaxants, the rabbit dose is typically 125% of that in mice. The mechanism of action was also confirmed in this test by observing train-of-four and tetanus fade, post-tetanic potentiation of single twitches and administration of the anticholinesterase drug neostigmine which reverses the relaxation. Reversibility, rapid onset and short duration are important factors to the anesthesiologist.

In Table I, the doses of the compounds of the invention are shown relative todoses of clinically available drugs. Clinically, 0.1 to 0.14 mg/kg of vecuronium has been used for endotracheal intubation, while 0.010 mg/kg is used for maintenance of relaxation. Therefore, as an estimate of the range of possible dosages which might be employed for the subject compounds, the ED90 would be doubled as an estimate for an intubating dose, while a dose 20 to 25% of the ED90 dose might be required for maintenance bolus doses. The clinical dose range might be between 29% to 200% of the estimated ED90.

TABLE I

| Neuromuscular Junction Blocking Activity (ED90 in mg/kg) | |
| --- | --- |
| Drug | Mouse |
| vercuronium | 0.03 |
| atracurium | 0.63 |
| Compound A | 10.00 |
| Compound B | 16.00 |
| Compound C | 16.00 |
| Compound D | 10.00 |
| Compound E | 3.98 |
| Compound F | 20.00 |
| Compound G | 20.00 |
| Compound H | 20.00 |
| Compound I | 10.00 |
| Compound J | 16.00 |
| Compound K | 16.00 |

The detailed pharmacologies in rabbits of three of the subject compounds are presented in Table II. The following is a brief description of the methodologies used in rabbits to describe neuromuscular blocking activity of the subject compounds. A more detailed description of these methods is presented in "Microcomputer Use in Measuring Onset, Duration, and Recovery from Non-Depolarizing Skeletal Muscle Relaxants in Rabbits", P.D. Thut et al., *Drug development Research* 5:182, 1985.

Male New Zealand white rabbits weighing between 2.5 and 3.4 kg were anesthetized with pentobarbital (30 mg/kg) and placed on their backs upon a 40° C. water filled temperature regulation pad. Following tracheostomy, the lungs were mechanically ventilated at 28 breaths per minute with room air, using an open system delivering 200 ml/stroke. This ventilation maintained $pCO_2$ at 38 $mmH_3$ and $pO_2$ at 85 mmHg. Direct arterial blood pressure was measured from the right common carotid artery. The test compounds were administered through a cannula placed in the marginal ear vein. Each foreleg was taped to a cushioned plate held in a femur clamp attached to the spinal board rack. The left central digit of each paw was connected to a force displacement transducer for measurement of muscle tension. Nerve stimulation was provided by pairs of pin electrodes placed on both sides of the ulnar nerve at the elbow of both forearms. The right ulnar nerve was stimulated at 1 Hz, 1 pps for 0.5 msec duration. The left ulnar nerve was similarly stimulated, every 15 seconds, with addition of interspersed trains-of-four and tetanizing stimuli. The parameters reported in Table II are: potency (ED90), which is the dose required to depress twitch tension to 10% of its control value; onset (T85%), which is the time from injection until 85% of the maximal drug effect is achieved; duration, which is the time from injection until the train-of-four has recovered to 75%; blood pressure (BP), which is the percentage change of pre-drug blood pressure; and heart rate (HR), which is the percentage change from pre-drug heart rate.

TABLE II

| Rabbit Paw Twitch Equi-efficacious Dose Data | | | | | |
| --- | --- | --- | --- | --- | --- |
| Compound | ED90 (mg/kg) | T85% (seconds) | Duration (minutes) | BP (% change) | HR (% change) |
| atracurium | 0.05 | 126.90 | 14.30 | −3.40 | −1.00 |
| vecuronium | 0.02 | 97.30 | 16.80 | 1.10 | −9.90 |
| pancuronium | 0.02 | 147.50 | 35.50 | 2.70 | 0.00 |
| Compound A | 9.92 | 27.40 | 16.10 | −22.00 | −7.90 |
| Compound B | 31.26 | 24.40 | 22.00 | −18.83 | 8.79 |
| Compound C | 19.80 | 28.90 | 15.10 | 3.40 | 6.50 |

In Tables I and II, the designated compounds are as follows:

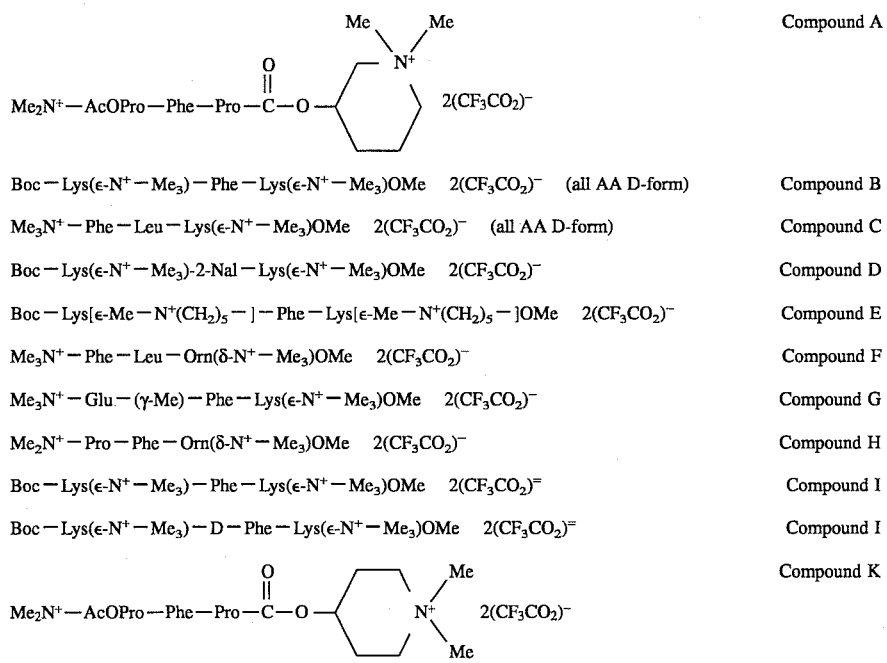

The results in the Tables show that the subject compounds, while not as potent as those utilized for comparison, are advantageous in that they have a significantly shorter onset of activity.

We claim:

1. A diquaternary peptide having the formula:

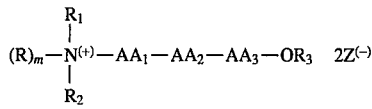

and

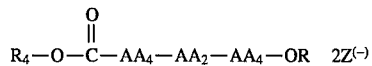

wherein:

R is lower alkyl;

$R_1$ and $R_2$ are lower alkyl or $R_1$ and $R_2$, together with the nitrogen to which they are attached form a heterocyclic ring having 5 to 7 member atoms;

$R_3$ is lower alkyl, [N,N-di(lower alkyl)-3-piperidinium]$^{(+)}$, or [N,N-di(lower alkyl)-4piperidinium]$^{(+)}$;

$R_4$ is selected from the group consisting of t-butyl, benzyl or fluorenylmethyl;

$AA_1$ is selected from the group consisting of trans-4-acetoxyproline, phenylalanine, glutamic acid-γ-methyl ester, or proline;

$AA_2$ is selected from the group consisting of phenylalanine, leucine, 3-(2-naphthyl)alanine, 3-(1-naphthyl)alanine, and 3-cyclohexylalanine;

$AA_3$ is proline when $R_3$ is [N,N-di(lower alkyl)-3-piperidinium]$^{(+)}$ or [N,N-di(lower alkyl)4-piperidinium]$^{(+)}$, and is Orn(δ-$N^{(+)}$—R—$R_1$—$R_2$) or Lys(ε-$N^{(+)}$—R—$R_1$—$R_2$) when $R_3$ is lower alkyl;

$AA_4$ is Orn(δ-$N^{(+)}$—R—$R_1$—$R_2$) or Lys(ε-$N^{(+)}$—R—$R_1$—$R_2$);

$Z^{(-)}$ is a pharmaceutically acceptable anion;

$(R)_m R_1 R_2 N^{(+)}$— represents the alpha amino group of $AA_1$; and m is 0 or 1, with the proviso that m is zero only when $AA_1$ is trans-4-acetoxyproline or proline.

2. A peptide in accordance with claim 1, wherein $R_1$ and $R_2$, together with the nitrogen to which they are attached, form a heterocyclic ring selected from the group consisting of pyrrolidine, piperidine, hexamethyleneimine, piperazine and morpholine.

3. A peptide in accordance with claim 1, consisting of N-α-t-butyloxycarbonyl-αS-4-[1-(1-methyl)piperidinium ]butyl}glycyl-L-phenylalanyl-α-S-{4--[1-(1-methyl)piperidinium]butyl}glycine.

4. A peptide in accordance with claim 1, consisting of the 1,1,-dimethyl-4-piperidinium ester of N,N-dimethyl-trans-4-acetoxy-L-prolyl-L-phenylalanyl-L-proline.

5. A peptide in accordance with claim 1, consisting of the methyl ester of N-α-t-butoxycarbonyl-L-($N^ε$, $N^ε$,$N^ε$-trimethyl)lysyl-L-phenylalanyl-L-( $N^ε$,$N^ε$,$N^ε$-trimethyl)lysine.

6. A peptide in accordance with claim 1, consisting of the methyl ester of N-α-t-butoxycarbonyl-N-L-($N^ε$,$N^ε$,$N^ε$-trimethyl)lysyl-L-2-naphthylalanyl-L-($N^ε$,$N^ε$,$N^ε$-trimethyl)lysine.

7. A pharmaceutical composition comprising a pharmaceutical carrier suitable for parenteral administration and a diquaternary peptide having the formula:

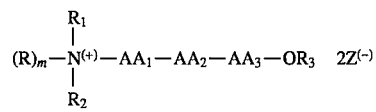

and

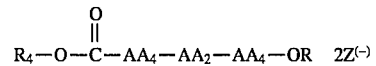

wherein:

R is lower alkyl;

$R_1$ and $R_2$ are lower alkyl or $R_1$ and $R_2$, together with the nitrogen to which they are attached form a heterocyclic ring having 5 to 7 member atoms;

$R_3$ is lower alkyl, [N,N-di(lower alkyl)-3-piperidinium]$^{(+)}$, or [N,N-di(lower alkyl)-4- piperidinium]$^{(+)}$;

$R_4$ is selected from the group consisting of t-butyl, benzyl or fluorenylmethyl;

$AA_1$ is selected from the group consisting of trans-4-acetoxyproline, phenylalanine, glutamic acid-γ-methyl ester, or proline;

$AA_2$ is selected from the group consisting of phenylalanine, leucine, 3-(2-naphthyl)alanine, 3-(1-naphthyl)alanine, and 3-cyclohexylalanine;

$AA_3$ is proline when $R_3$ is [N,N-di(lower alkyl)-3-piperidinium]$^{(+)}$ or [N,N-di(lower alkyl)-4-piperidinium]$^{(+)}$, and is Orn(δ-$N^{(+)}$—R—$R_1$—$R_2$) or Lys(ε-$N^{(+)}$—R—$R_1$—$R_2$) when $R_3$ is lower alkyl;

$AA_4$ is Orn(δ-$N^{(+)}$—R—$R_1$—$R_2$) or Lys(ε-$N^{(+)}$—R—$R_1$—$R_2$);

$Z^{(-)}$ is a pharmaceutically acceptable anion;

$(R)_m R_1 R_2 N^{(+)}$ represents the alpha amino group of $AA_1$; and m is 0 or 1, with the proviso that m is zero only when $AA_1$ is trans-4-acetoxyproline or proline.

8. A method of producing skeletal muscle relaxation in a mammal in need thereof which comprises administering to said mammal a pharmaceutically acceptable carrier and an effective amount of a diquaternary peptide of claim 1.

9. A method in accordance with claim 8, wherein $R_1$ and $R_2$, together with the nitrogen to which they are attached, form a heterocyclic ring selected from the group consisting of pyrrolidine, piperidine, hexamethyleneimine, piperazine and morpholine.

10. A method in accordance with claim 8, wherein said composition contains the 1,1-dimethyl-4-piperidinium ester of N,N-dimethyl-trans-4-acetoxy-L-prolyl-L-phenylalanyl-L-proline.

11. A method in accordance with claim 8, wherein said composition contains the methyl ester of N-α-t-butoxycarbonyl-L-($N^ε$,$N^ε$,$N^ε$-trimethyl)lysyl-L-phenylalanyl-L-$N^ε$-($N^ε$,$N^ε$-trimethyl)lysine or the methyl ester of N-α-t-butoxycarbonyl-N-L-($N^ε$,$N^ε$,$N^ε$-trimethyl)lysyl-L-2-naphthylalanyl-L-($N^ε$,$N^ε$,$N^ε$-trimethyl)lysine.

* * * * *